US006479441B1

(12) United States Patent
White

(10) Patent No.: US 6,479,441 B1
(45) Date of Patent: Nov. 12, 2002

(54) PROCESS FOR ENHANCING THE TRANSPARENCY OF TRANSPARENT SOAP BARS

(75) Inventor: J. Matthew White, Morrow, OH (US)

(73) Assignee: Cognis Corporation, Cincinnati, OH (US)

( * ) Notice: Subject to any disclaimer, the term of this patent is extended or adjusted under 35 U.S.C. 154(b) by 831 days.

(21) Appl. No.: 08/811,891

(22) Filed: Mar. 5, 1997

(51) Int. Cl.[7] .................................................. A61K 7/00
(52) U.S. Cl. ........................ 510/147; 510/141; 510/145
(58) Field of Search ................................ 510/141, 145, 510/147

(56) References Cited

U.S. PATENT DOCUMENTS 78,182 A * 5/1868 Brown et al. ............... 510/147
164,606 A * 6/1875 Strunz ........................ 510/147
4,256,600 A 3/1981 Lewis et al. ................ 252/132
4,490,280 A 12/1984 Joshi et al. ................. 252/368
4,988,453 A * 1/1991 Chambers et al. .......... 510/147
5,041,234 A * 8/1991 Instone et al. .............. 510/147

* cited by examiner

*Primary Examiner*—Necholus Ogden
(74) *Attorney, Agent, or Firm*—John E. Drach; Steven J. Trzaska

(57) ABSTRACT

A process for inhibiting the formation of surface haze on finished transparent soap bars involving the steps of: (a) providing a finished transparent soap bar; (b) providing a coating component selected from the group consisting of water, a $C_1$–$C_8$ aliphatic alcohol, a polyol, and mixtures thereof; (c) applying the coating component onto the finished transparent soap bar to form a coated transparent soap bar; and (d) immediately packaging the coated transparent soap bar.

10 Claims, No Drawings

PROCESS FOR ENHANCING THE TRANSPARENCY OF TRANSPARENT SOAP BARS

FIELD OF THE INVENTION

The present invention generally relates to transparent soap bars. More particularly, the present invention is directed to a process for inhibiting the formation of surface haze on transparent soap bars.

BACKGROUND OF THE INVENTION

Transparent soap bars are normally milder than opaque bars. These soaps depend for their distinctive appearance upon the fact that soap is deposited from alcoholic solution in a transparent, ultramicrocrystalline form. The incorporation of glycerol and sugars also tend to cause soap to assume this form. The effect is entirely physical, and depends upon the conditions under which the soap crystallizes rather than the presence of alcohol or any other substance in the finished soap cake. Thus, a transparent soap made with the aid of alcohol retains its appearance after most of the alcohol has been evaporated from it.

Transparent soaps vary greatly in composition. They may be prepared simply by dissolving soap flakes in alcohol and then driving off the greater part of the alcohol. Such a product will not be greatly different in composition from the original soap flakes. A more usual method of manufacture, however, is to add alcohol and glycerol, in the proportion of about two parts of alcohol to one of glycerol, to a hot saponified batch of semi-boiled soap until a rapidly cooled sample is clear, after which the batch is framed in the usual way. Sugar may also be added. The fats used in transparent soaps usually are tallow and coconut oil. Up to about 30% castor oil is often used in the fat charge, as the presence of this oil reduces the amount of alcohol, glycerol or sugar required to render the soap transparent. The anhydrous soap content of transparent soaps is usually well under 50%.

A problem encountered in the production of transparent soap bars relates to the formation of a haze on the surface of the bars after they are packaged and stored. The haze is believed to be caused by the absorption of atmospheric moisture into the transparent bars during storage.

SUMMARY OF THE INVENTION

The present invention relates to a process for inhibiting the formation of surface haze on transparent soap bars involving the steps of:

(a) providing a finished transparent soap bar;

(b) providing a coating component selected from the group consisting of water, a $C_1$–$C_8$ aliphatic alcohol, a polyol, and mixtures thereof;

(c) applying the coating component onto the finished transparent soap bar to form a coated transparent soap bar; and (d) immediately packaging the coated transparent soap bar.

DESCRIPTION OF THE INVENTION

Other than in the operating examples, or where otherwise indicated, all numbers expressing quantities of ingredients or reaction conditions used herein are to be understood as being modified in all instances by the term "about".

For purposes of this invention, a soap bar is deemed to be transparent when 12 pt type is readable through a one inch thick bar. Transparent soaps vary greatly in composition. They may be prepared simply by dissolving soap flakes in alcohol and then driving off the greater part of the alcohol. Such a product will not be greatly different in composition from the original soap flakes. A more usual method of manufacture, however, is to add alcohol and glycerol, in the proportion of about two parts of alcohol to one of glycerol, to a hot saponified batch of semi-boiled soap until a rapidly cooled sample is clear, after which the batch is framed in the usual way. Sugar may also be added. The fats used in transparent soaps usually are tallow and coconut oil. Up to about 30% castor oil is often used in the fat charge, as the presence of this oil reduces the amount of alcohol, glycerol or sugar required to render the soap transparent. The anhydrous soap content of transparent soaps is usually well under 50%. The precise composition of a transparent soap bar is unimportant for purposes of the present invention, i.e., the soap bar need only be transparent once it is finished/stamped.

It has been surprisingly found that by coating a finished transparent soap bar, prior to packaging, with a coating component selected from the group consisting of water, $C_1$–$C_8$ aliphatic alcohols, polyols, and mixtures thereof, the formation of surface haze which occurs during storage of the soap bars can be successfully inhibited, thereby enhancing the transparency of the transparent soap bars over prolonged periods of time.

The alcohols which may be employed in the process of the present invention fall into two general categories: (1) short-chain aliphatic alcohols, and (2) polyols.

The short-chain aliphatic alcohols are those having from 1 to about 8 carbon atoms, and may be either paraffinic or olefinic. Examples of short-chain aliphatic alcohols which may be used include, methanol, ethanol, propanol, and allyl alcohol.

The polyol component of the coating component according to the invention can be any aliphatic compound having 2 or more alcohol functionalities. Such polyols include diols, triols, tetraols, etc. Examples of such polyols include, but are not limited to, ethylene glycol, 1,2-propylene glycol, 1,3-propylene glycol, diethylene glycol, dipropylene glycol, triethylene glycol, 1,6-hexylene glycol, glycerine, polyglycerols, monosaccharides such as glucose or fructose, disaccharides such as sucrose, sorbitol, and polyvinyl alcohol. Preferred polyols include 1,2-propylene glycol, glycerine, polyglycerol, and sorbitol. The most preferred polyol is glycerine.

In a preferred embodiment of the present invention, the coating component consists of a mixture of water and a polyol, preferably glycerin, in a ratio by weight of 1:1.

The process of the present invention involves coating a finished transparent soap bar with the above-disclosed coating component. For purposes of the present invention, a finished transparent soap bar is one which has been formulated, refined, plodded and stamped into a ready-to-use toilet bar.

The coating step may be performed in any conventional manner such as by dipping, rinsing or spraying the finished transparent soap bar.

Once the bar has been coated with the above-disclosed coating component, it is then packaged, and ready to be shipped to consumers. It is important to note that the coated transparent soap bar must be packaged immediately after coating so as to preclude the coating component from evaporating into the atmosphere.

The present invention will be better understood from the examples which follow, all of which are meant to be illustrative only and are not meant to unduly limit the scope of the invention in any way. Unless otherwise indicated, percentages are on a weight-by-weight basis.

EXAMPLES

1. A transparent soap bar which had developed surface haze in its packaging was removed from its packaging and coated with a thin layer of E-918 glycerin. The surface haze disappeared, the bar was repackaged and remained clear for over 3 years.
2. Transparent soap bars, upon standing in the molds, developed a surface haze. The bars were removed from the molds and coated with a thin layer of E-918 glycerin. The surface haze disappeared, the bars were repackaged and remained clear for over 18 months.

What is claimed is:

1. A process for inhibiting the formation of surface haze on finished transparent soap bars comprising:

(a) providing a finished transparent soap bar;

(b) providing a coating component selected from the group consisting of water, a $C_1$–$C_8$ aliphatic alcohol, a polyol, and mixtures thereof;

(c) applying the coating component onto the finished transparent soap bar to form a coated transparent soap bar; and (d) immediately packaging the coated transparent soap bar.

2. The process of claim 1 wherein the polyol is glycerin.

3. The process of claim 2 wherein the coating component is a 1:1 mixture of water and glycerin.

4. The process of claim 1 wherein the coating component is water.

5. The process of claim 1 wherein the coating component is a $C_1$–$C_8$ aliphatic alcohol.

6. The product of the process of claim 1.

7. The product of the process of claim 2.

8. The product of the process of claim 3.

9. The product of the process of claim 4.

10. The product of the process of claim 5.

* * * * *